United States Patent [19]

Gordon et al.

[11] Patent Number: 4,490,254
[45] Date of Patent: Dec. 25, 1984

[54] BLOOD FILTER

[75] Inventors: Lucas S. Gordon, San Juan Capistrano; Karl M. Sutherland, Westminster, both of Calif.

[73] Assignee: Bentley Laboratories, Inc., Irvine, Calif.

[21] Appl. No.: 124,312

[22] Filed: Feb. 25, 1980

[51] Int. Cl.³ .................. B01D 35/00; B01D 19/02
[52] U.S. Cl. .................. 210/247; 210/304; 210/436; 210/927
[58] Field of Search ........... 210/927, 436, 443, 493, 210/497.01, 499, 497.1, 456, 304, 247

[56] References Cited

U.S. PATENT DOCUMENTS

| | | | |
|---|---|---|---|
| 1,175,948 | 3/1916 | French | 210/304 |
| 3,056,499 | 10/1962 | Liddel | 210/456 X |
| 3,728,256 | 4/1973 | Cooper | 210/456 X |
| 3,935,106 | 1/1976 | Lipner | 210/436 |
| 4,038,194 | 7/1977 | Luceyk et al. | 210/927 |
| 4,164,468 | 8/1979 | Raible | 210/436 |

*Primary Examiner*—Frank Spear
*Attorney, Agent, or Firm*—Lyon & Lyon

[57] ABSTRACT

This invention relates to a blood filter assembly in which blood enters at the bottom end of the assembly, is directed in spirally upward path and then passes through a filter medium. After passing through the filter medium, the blood flows downwardly out of an outlet in the bottom end of the assembly. A gas vent is provided at the top end of the assembly. In its preferred embodiment, the outer shell of the assembly tapers from the bottom end to a narrower diameter top end, the filter medium is generally shaped in the form of a cylindrical tube and a core member is provided radially inwardly of said filter medium and spaced therefrom. This filter assembly is particularly useful for the removal of particulate matter, gas and other foreign materials from blood.

8 Claims, 4 Drawing Figures

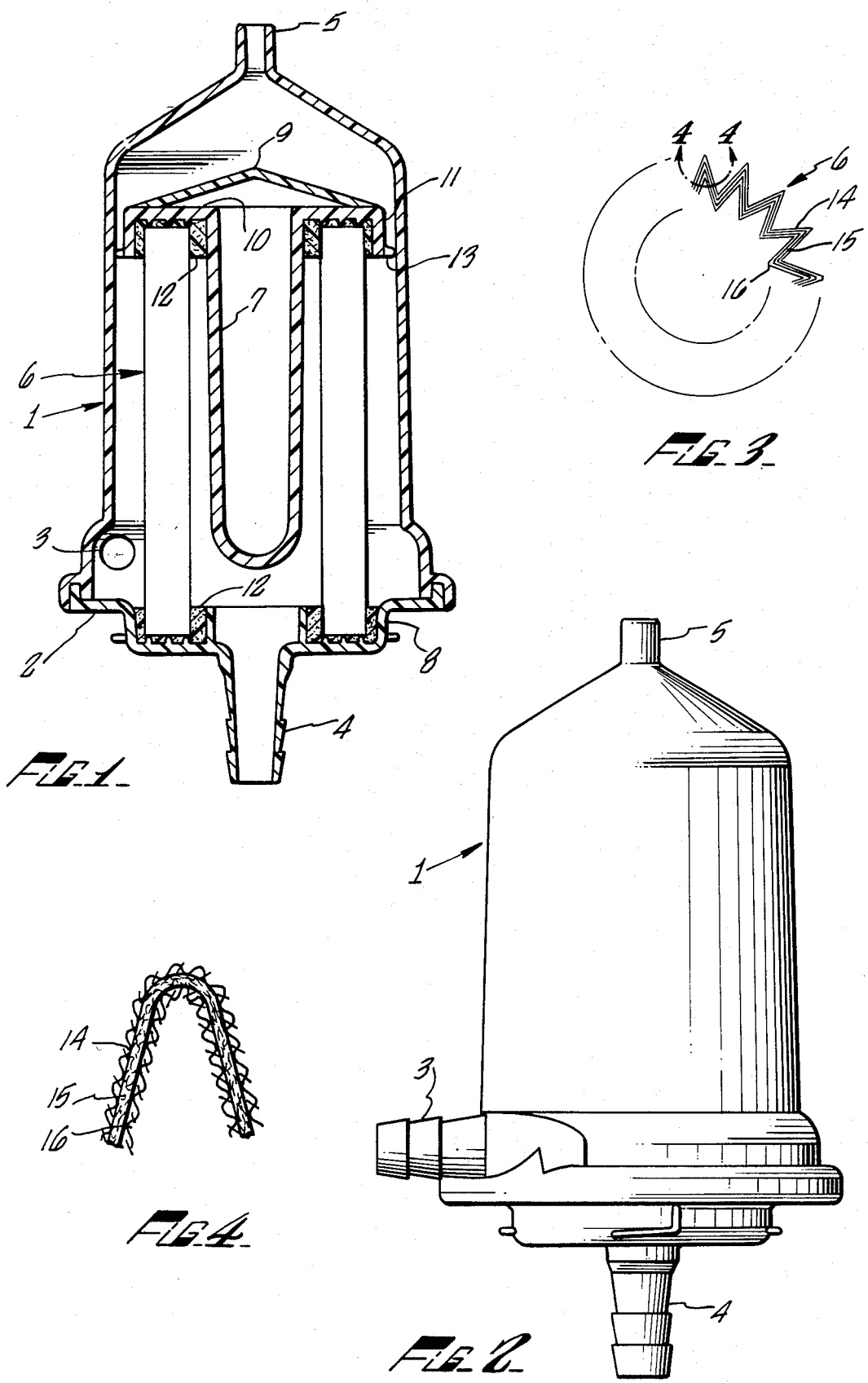

BLOOD FILTER

BACKGROUND OF THE INVENTION

It is frequently desirable in medical practice to cause blood to flow through an extracorporeal circuit, e.g., during surgery, dialysis, etc. When this is done, the blood may come to contain undesirable foreign matter, e.g., tissue or bone debris resulting from surgery or injury, gas bubbles, clots, or other matter which it is desirable to remove from the blood before it returns to the body.

There are several blood filter assembly structures known to and/or used by the art. Among these are Esmond U.S. Pat. No. 3,795,088, Luceyk et al. U.S. Pat. No. 4,038,194 and Mouwen U.S. Pat. No. 4,056,476, the disclosures of which are incorporated by reference herein. Other known blood filters are disclosed in U.S. Pat. Nos. 3,457,339; 3,696,932 and 3,701,433, the disclosures of which are also incorporated herein by reference.

SUMMARY OF THE INVENTION

Unlike the typical blood filter assembly in use today, the present invention does not have the blood inlet at or near one end of the assembly and the blood outlet at or near the other end. Rather, the assembly of the present invention provides a blood inlet in the region of the bottom end of the assembly and the blood outlet at the bottom end of the assembly as well. The blood inlet is located such that the incoming blood is directed against the inner wall of the tubular shell of the assembly such that the blood follows a spirally upward path within the shell. The blood then passes through a filter medium which is spaced radially inwardly from the shell and is of a generally tubular configuration. After passing inwardly through the filter medium, the blood flows downwardly and out of the assembly through an outlet in the bottom wall thereof. The location of the blood inlet at the bottom end of the filter assembly facilitates the removal of gas bubbles because they can rise upwardly and out of the blood rather than being carried downwardly in an entrained condition as is the case with blood assemblies having a top-end inlet. The design of the present blood filter assembly also makes it possible to provide a relatively large volume on the outside of the filter which in turn provides space for gas contained in the blood to escape into when the vent is closed or clogged.

In addition, the spiral flow of the incoming blood reduces the risk of blood damage because the blood is not required to fall through a space between the inlet and the filter medium as is the case with some top-end assemblies and because the smooth flow path does not require the blood to encounter sharp edges or abrupt changes in direction.

The blood filter medium which may be used in the assembly of the present invention may be of any of a variety of constructions, e.g., foam, fabric or other. However, the preferred medium is nylon monofilaments woven in a regular, even-sided two up and two down twill weave having an average pore size in the range of 23 to 27 microns and a nominal pore size of 25 microns. The nylon yarn preferably has a nominal diameter of 32 microns and the diameter is preferably in the range of 30 to 36 microns.

In the preferred embodiment of the present invention, the filter medium is generally in the shape of a cylindrical tube, the conically shaped shell tapers from a wider diameter bottom end to a narrower diameter top end and a cylindrical core member is positioned inside of the filter medium and spaced therefrom.

IN THE DRAWING

FIG. 1 shows an axial cross-sectional view of the blood filter assembly.

FIG. 2 shows an exterior view of the assembly.

FIGS. 3 and 4 show the details of the filter medium construction.

Referring now to the drawings in more detail, it can be seen from FIG. 1 that the assembly comprises a shell 1, a bottom wall 2 and is provided with blood inlet 3, blood outlet 4 and gas vent 5. Positioned between the blood inlet and the blood outlet is filter medium 6 and positioned within the filter medium is core 7. Bottom wall 2 is provided with recess 8 to accommodate the filter medium 6 and cap member 9 rests upon flange 10 of core 7. Flange 10 is provided with lip 11 which also functions to hold and position filter medium 6. Filter medium 6 is secured in flange 10 and bottom wall 2 by a suitable potting compound or adhesive 12. Lip 11 is provided with spaced tabs 13 which function to center the upper end of the filter medium in shell 1. In the preferred embodiment shown in FIG. 1, the filter medium has a generally cylindrically tubular shape and the radially outwardly positioned shell wall tapers from the larger diamater bottom end toward the smaller diameter top end. The location of blood inlet 3 is such that the incoming blood is directed along a spirally upward path by the inner wall of the shell. As shown in FIG. 2, the blood inlet 3 is positioned such that the incoming blood enters in a generally tangential direction.

The blood then passes through the filter medium 6 where foreign materials are removed. The filtered blood then passes downwardly through the space between the filter medium 6 and the core 7 and finally out of the filter assembly through outlet 4.

Core 7 also functions to reduce the amount of priming fluid required during start-up.

Gas which has been removed from the blood rises upwardly through the assembly and exits through vent 5.

The detailed construction of the filter medium 6 is shown in FIGS. 3 and 4. As indicated in FIG. 3, the filter medium is pleated and the cylindrical filter medium constitutes, in the preferred embodiment of the invention, a series of parallel pleats. In addition, in the preferred embodiment of the invention, the woven filter is supported between an inner and an outer polypropylene net. Referring to FIGS. 3 and 4, the polypropylene nets are indicated by numerals 14 and 15, respectively, and sandwiched between them is the woven filter 16. The polypropylene nets 14 and 15 serve to rigidify the filter structure.

It will, of course, be understood by those skilled in the art that other filter materials, e.g., woven polyester monofilament yarns or other yarns which will not degrade or have a deleterious effect on the blood or foam materials such as polyurethane foams or other known filter media which have proved suitable for blood filtration, may be used. Similarly, when woven yarns are used, various weave constructions other than those specifically set forth herein may be used without departing from the present invention.

Having fully described the present invention, it is to be understood that it is not limited to the specific embodiments set forth above, but rather is of the full scope of the appended claims.

We claim:
1. Blood filter assembly comprising:
   a. a shell having a first top end and a second bottom end,
   b. a blood inlet located in the region of said bottom end and opening into said bottom end,
   c. a blood outlet located in the region of said bottom end,
   d. a gas vent located in the region of said top end, and
   e. a blood filter medium located between said blood inlet and said blood outlet,
   said blood inlet being located and configured in a manner capable of directing incoming blood in a generally spiral path within said shell.

2. The assembly of claim 1 wherein said shell is tubular in shape and said filter medium is generally tubular in a shape.

3. The assembly of claim 2 where said shell tapers from a wider diameter bottom end to a more narrow diameter top end.

4. The assembly of claim 3 wherein a core member is provided radially inwardly from and spaced from said filter medium.

5. The assembly of claim 3 wherein said filter medium is generally cylindrical in shape.

6. The assembly of claim 1 wherein said filter medium comprises a woven filter material sandwiched between layers of stiff netting material.

7. The assembly of claim 6 wherein said filter medium is pleated.

8. The assembly of claim 1 wherein the space between said shell and said filter medium gradually decreases from the region of the bottom end to the region of the top end.

* * * * *